United States Patent
Hayashi et al.

(10) Patent No.: US 10,281,452 B2
(45) Date of Patent: May 7, 2019

(54) BLOOD COAGULATION SYSTEM ANALYZER, BLOOD COAGULATION SYSTEM ANALYSIS METHOD AND PROGRAM

(71) Applicant: Sony Corporation, Tokyo (JP)

(72) Inventors: Yoshihito Hayashi, Chiba (JP); Marc-Aurele Brun, Tokyo (JP); Isao Uchimura, Kanagawa (JP)

(73) Assignee: Sony Corporation, Tokyo (JP)

( * ) Notice: Subject to any disclaimer, the term of this patent is extended or adjusted under 35 U.S.C. 154(b) by 538 days.

(21) Appl. No.: 14/391,090

(22) PCT Filed: Mar. 5, 2013

(86) PCT No.: PCT/JP2013/001359
§ 371 (c)(1),
(2) Date: Oct. 7, 2014

(87) PCT Pub. No.: WO2013/153735
PCT Pub. Date: Oct. 17, 2013

(65) Prior Publication Data
US 2015/0077144 A1 Mar. 19, 2015

(30) Foreign Application Priority Data
Apr. 13, 2012 (JP) ................................. 2012-091947

(51) Int. Cl.
*G01N 27/02* (2006.01)
*G01N 27/06* (2006.01)
(Continued)

(52) U.S. Cl.
CPC ..... *G01N 33/48707* (2013.01); *G01N 27/026* (2013.01); *G01N 27/06* (2013.01); *G01N 33/4905* (2013.01)

(58) Field of Classification Search
CPC combination set(s) only.
See application file for complete search history.

(56) References Cited

U.S. PATENT DOCUMENTS

| | | | |
|---|---|---|---|
| 2002/0010553 A1* | 1/2002 | Givens | G01N 33/4905 702/22 |
| 2004/0147032 A1 | 7/2004 | Martin et al. | |

(Continued)

FOREIGN PATENT DOCUMENTS

| | | |
|---|---|---|
| CN | 102308203 | 1/2012 |
| EP | 2074430 B1 | 3/2011 |

(Continued)

OTHER PUBLICATIONS

Hayashi, Yoshihito, et al. "Dielectric coagulometry: a new approach to estimate venous thrombosis risk." Analytical chemistry 82.23 (2010): 9769-9774 (Hayashi 2010).*

(Continued)

*Primary Examiner* — Christian Jang
*Assistant Examiner* — Mitchell E Alter
(74) *Attorney, Agent, or Firm* — K&L Gates LLP

(57) ABSTRACT

There is provided a blood coagulation system analyzer, including a measurement section and an analysis section. The measurement section measures a time change of impedance of a blood sample, which is obtainable by applying an alternating electric field to the blood sample. The analysis section extracts a parameter indicating the characteristics of the impedance from the measured data of the time change of the impedance. Furthermore, the analysis section analyzes a degree of enhancement of blood coagulation on the basis of a comparison of the extracted parameter with at least one reference value which defines the criteria of the enhancement of blood coagulation.

34 Claims, 10 Drawing Sheets

(51) Int. Cl.
*G01N 33/49* (2006.01)
*G01N 33/487* (2006.01)

(56) References Cited

U.S. PATENT DOCUMENTS

| | | | |
|---|---|---|---|
| 2005/0015000 | A1 | 1/2005 | Djennati et al. |
| 2012/0035450 | A1* | 2/2012 | Hayashi ............ G01N 33/4905 600/369 |
| 2012/0048732 | A1 | 3/2012 | Hayashi et al. |
| 2014/0367261 | A1 | 12/2014 | Chen et al. |

FOREIGN PATENT DOCUMENTS

| | | |
|---|---|---|
| EP | 2 375 244 | 10/2011 |
| EP | 2 395 353 | 12/2011 |
| JP | H10-185926 A | 7/1998 |
| JP | 2002-238556 A | 8/2002 |
| JP | 2006-527363 A | 11/2006 |
| JP | 2010-501072 A | 1/2010 |
| JP | 2010-181400 | 8/2010 |
| JP | 2010-184100 A | 8/2010 |
| JP | 2011-257403 A | 12/2011 |
| JP | 2012-052906 | 3/2012 |
| JP | 2012-181400 | 9/2012 |
| JP | 2012-194087 | 10/2012 |

OTHER PUBLICATIONS

Zhou R, Chang B, Chang H. Impedance Analysis of Blood Coagulation by Prothrombin Time Assay in a Miniature Device. ASME. International Conference on Nanochannels, Microchannels, and Minichannels, ASME 3rd International Conference on Microchannels and Minichannels, Parts A and B: pp. 737-741.*

Office Action issued in CN Application 201380018666.3, dated Sep. 22, 2015 (22 pages).

Yoshihito Gatasgum et al., "Dielectric Coagulometry: A New Approach to Estimate Venous Thrombosis Risk", Analytical Chemistry, vol. 82, No. 23, Dec. 1, 2010 (9769-9774); American Chemical Society, Published on Web Oct. 29, 2010.

European Office Action dated Mar. 15, 2018 in corresponding EP Application No. 13 711 748.7.

Office Action received in JP application 2012091947, dated Feb. 23, 2016, 8 pages.

* cited by examiner

IP Interstitial pneumonia
LK Lung cancer
COPD Chronic obstructive pulmonary disease
CVD Collagen vascular disease
SAS Sleep apnea syndrome
infection Infections (such as pneumonia)
normal Healthy controls

FIG.14

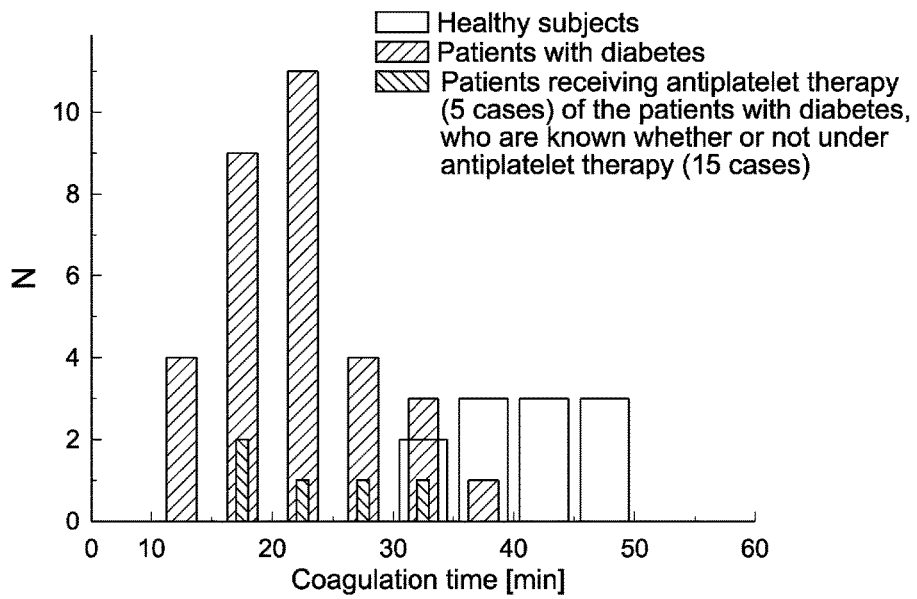

FIG.15

Healthy subjects:
    Mean value 40. 4min    Standard deviation 5. 7min

Respiratory, patients developing venous thromboembolism:
    Mean value 17. 5min    Standard deviation 2. 1min Orthopedic, whole group of patients:
    Mean value 20. 5min    Standard deviation 3. 0min Orthopedic, patients developing venous thromboembolism:
    Mean value 20. 4min    Standard deviation 3. 1min Whole group of patients with diabetes:
    Mean value 21. 4min    Standard deviation 5. 9min

BLOOD COAGULATION SYSTEM ANALYZER, BLOOD COAGULATION SYSTEM ANALYSIS METHOD AND PROGRAM

CROSS REFERENCES TO RELATED APPLICATIONS

The present application is a national stage of International Application No. PCT/JP2013/001359 filed on Mar. 5, 2013 and claims priority to Japanese Patent Application No. 2012-091947 filed on Apr. 13, 2012, the disclosure of which is incorporated herein by reference.

BACKGROUND

The present disclosure relates to an analyzer for analyzing a blood sample having a blood coagulation system disease, a method of the analysis, and a program therefor.

From the past, for example, to patients and healthy subjects at risk of thrombosis, prophylactic administration of an anti-platelet aggregation drug or an anticoagulant has been carried out. The patients at risk of thrombosis include but are not limited to, for example, patients with diabetes, atherosclerosis, cancer, heart disease, respiratory disease and the like, perioperative patients, and patients taking immunosuppressive drugs. In addition, the healthy subjects at risk of thrombosis include pregnant women and elderly people. Acetylsalicylic acid or the like is used as the anti-platelet aggregation drug. Warfarin, heparin, an activated blood coagulation factor X (Factor Xa) inhibitor or the like is used as the anticoagulant.

In the prophylactic administration of the anti-platelet aggregation drug or the anticoagulant against the thrombosis, there is a side effect that excessive dosages would increase the bleeding risk. To obtain a sufficient prophylactic effect with prevention of this side effect, the administration of medication in which the blood coagulation ability of the drug recipient is timely evaluated and the drug and the dosage is properly selected and set, is necessary.

As blood coagulation tests, there are methods such as prothrombin time-international normalized ratio (PT-INR) and activated partial thromboplastin time (APTT). As a platelet aggregation test, there is a method in which a substance that induces platelet aggregation is added to platelet rich plasma (PRP) obtained by centrifugation of blood, then a change in the light transmittance or the light absorbance associated with the aggregation is measured, which allows the acceptability of the aggregation activity to be determined.

In relation to the present disclosure, Patent Document 1 discloses a technique to acquire information relating to blood coagulation from the permittivity of blood, and describes a "blood coagulation system analyzing device having a pair of electrodes, an applying section that applies an alternating voltage to the pair of electrodes at a predetermined time interval, a measuring section that measures the permittivity of blood disposed between the pair of electrodes, and an analyzing section that analyzes the degree of the action of the blood coagulation system by using the permittivity of the blood measured at the time interval after the effect of an anticoagulant on the blood is released." This blood coagulation system analyzing device is capable of analyzing the early action of the blood coagulation system on the basis of a time change of the permittivity before the start timing of coagulation of the blood in terms of dynamics of viscoelasticity.

CITATION LIST

Patent Literature

PTL 1: Japanese Patent Application Laid-open No. 2010-181400

SUMMARY

Technical Problem

The blood coagulation test method such as PT-INR and APTT, of the related art, is substantially only capable of evaluating the bleeding risk associated with a lowering of the blood coagulation due to excessive administration of the anticoagulant.

In view of the circumstances as described above, it is desirable to provide a blood coagulation system analyzer, a blood coagulation system analysis method and a program therefor, capable of evaluating the risks due to enhancement of blood coagulation appropriately.

Solution to Problem

According to an embodiment of the present disclosure, there is provided a blood coagulation system analyzer including a measurement section and an analysis section. The measurement section measures a time change of impedance of a blood sample, which is obtainable by applying an alternating electric field to the blood sample. The analysis section is configured to extract a parameter indicating the characteristics of the impedance from the measured data of the time change of the impedance. Furthermore, the analysis section is configured to analyze a degree of enhancement of blood coagulation on the basis of a comparison of the extracted parameter with at least one reference value which defines the criteria of the enhancement of blood coagulation.

Since the analysis section analyzes the degree of enhancement of blood coagulation based on the time change of impedance of the blood sample, it is possible to appropriately evaluate the risks associated with it.

The measurement section may calculate permittivity on the basis of the measured impedance and obtain a time change of the permittivity. In addition, the analysis section may perform the analysis using a characteristic time, which is the time indicating the characteristics of the permittivity, as the parameter.

The analysis section may obtain the characteristic time of a healthy subject and obtain one of the time of 2/3 or more and 3/3 or less of the characteristic time of the healthy subject as the reference value. This allows it to lead to more certainty of the evaluation of the risks associated with the blood coagulation.

The analysis section may obtain reference values which are set by a plurality of stages as the reference values. This allows it to evaluate the risks associated with the blood coagulation in stages. In this case, the analysis section may obtain the characteristic time of a healthy subject and obtain a plurality of the time of 2/3 or more and 3/3 or less of the characteristic time of the healthy subject as the reference values.

The analysis section may target as a determination target the blood sample collected from a patient having respiratory disease, diabetes, or other internal disease.

The analysis section may obtain the characteristic time of a healthy subject and obtain one of the time of 23/30 or more and 30/30 or less of the characteristic time of the healthy subject as the reference value. This allows it to lead to more certainty of the evaluation of the risks associated with the blood coagulation.

The analysis section may obtain the characteristic time of a healthy subject and obtain a plurality of the time of 23/30 or more and 30/30 or less of the characteristic time of the healthy subject as the reference values. This allows it to evaluate the risks associated with the blood coagulation in stages.

The analysis section may target as a determination target the blood sample collected from a patient who has undergone an artificial knee joint replacement or other surgery, or collected from a patient taking an antiplatelet drug or an anticoagulant.

The measurement section may obtain data of the time change of the permittivity, including a first upper peak area which is an early peak area and a second upper peak area which is the next peak area of the first upper peak area. The analysis section may employ as the characteristic time a coagulation time which is the time at which the second upper peak area is possible to be reached.

Otherwise, the measurement section may obtain data of the time change of the permittivity in ramp form, including a first permittivity area and a second permittivity area having higher permittivity than the first permittivity area. Then, the analysis section may employ as the characteristic time a coagulation time which is the time at an intersection of a first extrapolation line and a second extrapolation line. The first extrapolation line is inserted in such a way that the slope thereof becomes the maximum at the interval between the first and the second permittivity areas. The second extrapolation line is inserted in such a way that the slope thereof becomes the minimum at the second permittivity area.

Since such a coagulation time at which the second upper peak area regarding the permittivity is possible to be reached is closely related to the enhancement of the blood coagulation, by using this as the parameter, it is possible to increase the certainty of the evaluation of the risks due to the hypercoagulable state.

The measurement section may obtain data of the time change of the permittivity, including a first lower peak area after a first upper peak area which is an early peak area, a second upper peak area which is the next peak area of the first upper peak area, and a main linear part between the first lower peak area and the second upper peak area. The analysis section may employ as the characteristic time a start time of the main linear part.

Otherwise, the measurement section may obtain data of the time change of the permittivity in ramp form, including a first permittivity area and a second permittivity area having higher permittivity than the first permittivity area. Then, the analysis section may employ as the characteristic time a start time of an overlap between an extrapolation line and a curve of the time change of the permittivity. The extrapolation line is one inserted in such a way that the slope thereof becomes the maximum at the interval between the first and the second permittivity areas.

Since such a start time of the main linear part is also closely related to the enhancement of the blood coagulation, by using this as the parameter, it is possible to increase the certainty of the evaluation of the risks due to the hypercoagulable state.

The measurement section may measure the time change of impedance of the blood sample to which the alternating electric field, having a frequency of 2 MHz or more and 40 MHz or less, or 300 kHz or more and 3 MHz or less, is applied.

The analysis section may obtain, as the at least one reference value, at least one selected from the group consisting of the mean value, the standard deviation, the median, the maximum value and the minimum value, of the parameter in each of a healthy subject and a patient. By that the statistical value of the parameter is set as the reference value, it is possible to increase the certainty of the evaluation of the risks due to the hypercoagulable state.

The measurement section may measure the time change of impedance of the blood sample, which is obtainable by applying the alternating electric field to the blood sample collected from a patient taking an anti-platelet aggregation drug or an anticoagulant.

According to another embodiment of the present disclosure, there is provided a blood coagulation system analysis method including applying an alternating electric field to a blood sample.

A time change of impedance of the blood sample obtained by the application of the alternating electric field is measured.

A parameter indicating the characteristics of the impedance from the measured data of the time change of the impedance is extracted. A degree of enhancement of blood coagulation is analyzed on the basis of a comparison of the extracted parameter with at least one reference value which defines the criteria of the enhancement of blood coagulation.

According to still another embodiment of the present disclosure, there is provided a program configured to cause a computer to perform the following processes.

It includes a process of measuring a time change of impedance of a blood sample which is obtainable by applying an alternating electric field to the blood sample.

It further includes a process of extracting a parameter indicating the characteristics of the impedance from the measured data of the time change of the impedance, and analyzing a degree of enhancement of blood coagulation on the basis of a comparison of the extracted parameter with at least one reference value which defines the criteria of the enhancement of blood coagulation.

According to a further embodiment of the present disclosure, a blood coagulation system analyzer comprises a blood measurement section configured to measure an impedance of a blood sample and a blood analysis section configured to determine a degree of blood coagulation based on the impedance. In this further embodiment, the blood analysis section is configured to determine the degree of blood coagulation by comparing a blood coagulation time based on the impedance to a reference blood coagulation time defined so as to distinguish between a healthy subject and a subject with a medical condition. In this embodiment, the reference blood coagulation time is between a first mean time including a first standard deviation time associated with blood coagulation of the healthy subject and a second mean time including a second standard deviation time associated with blood coagulation of the subject with the disease.

According to an additional embodiment of the present disclosure, a method of determining a degree of blood coagulation comprises measuring an impedance of a blood sample and determining the degree of blood coagulation based on the impedance.

Advantageous Effects of Invention

As described above, according to the present disclosure, it is possible to evaluate the risks due to enhancement of blood coagulation appropriately.

Additional features and advantages are described herein, and will be apparent from the following Detailed Description and the figures.

BRIEF DESCRIPTION OF THE FIGURES

FIG. 14 shows a frequency distribution of the coagulation time in healthy subjects and patients with diabetes.

FIG. 15 shows the mean values and the standard deviations of the coagulation time in healthy subjects and patients with each disease.

DETAILED DESCRIPTION

Hereinafter, embodiments of the present disclosure will be described with reference to the drawings.

1. Configuration of Blood Coagulation System Analyzer

Figure 1:
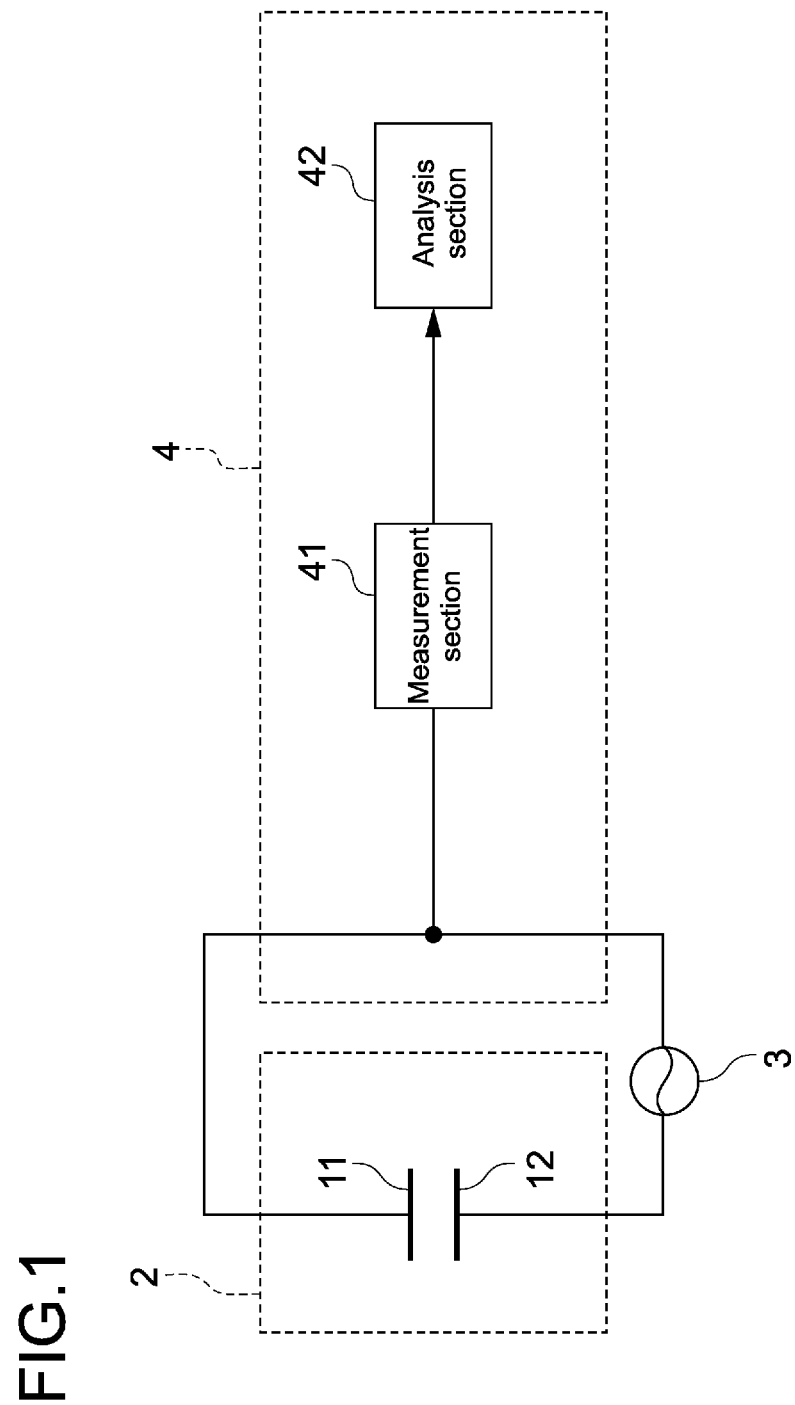
FIG. 1 shows a functional schematic configuration of a blood coagulation system analyzer according to an embodiment of the present disclosure.

FIG. 1 shows a functional schematic configuration of a blood coagulation system analyzer according to an embodiment of the present disclosure.

The blood coagulation system analyzer includes a sample cartridge 2 to hold a sample of blood, a pair of electrodes 11 and 12 to apply a voltage to the blood held in the sample cartridge 2, and a power supply 3 to apply an AC (alternating-current) voltage to the electrodes 11 and 12. Further, the blood coagulation system analyzer includes a measurement section 41 to measure the permittivity of the blood and an analysis section 42 to receive the output of the information indicating the measurement result from the measurement section 41 and determine the blood coagulation ability. By the measurement section 41 and the analysis section 42, a signal processing section 4 is configured.

In the sample cartridge 2, a drug introduction port for adding a platelet activator or the like to the held blood sample (hereinafter referred to as "blood", unless otherwise necessary) may be provided. The blood may be housed in the sample cartridge 2 after being premixed with the platelet activator or the like.

The power supply 3 applies the voltage from the timing when an order to start measurement is received or the timing when the power is turned on, as the start timing. Specifically, the power supply 3 applies an AC voltage having a predetermined frequency to the electrodes 11 and 12 at set measurement intervals. Thus, an alternating electric field having the predetermined frequency is applied to the blood.

The measurement section 41 measures the complex permittivity, the frequency dispersion thereof and the like, at a predetermined cycle, from the timing when an order to start measurement is received or the timing when the power is turned on, as the start timing. That is, as will be described later, the measurement section measures a three-dimensional complex permittivity spectrum which involves time axis. Specifically, for example if the permittivity is measured, the measurement section 41 measures the current or impedance between the electrodes 11 and 12 at the predetermined cycle and calculates the permittivity from measurement values. In the calculation of the permittivity, known function and relational expression showing the relationship between the current or impedance and the permittivity is used.

To the analysis section 42, data of the calculated permittivity are given from the measurement section 41 at measurement intervals. In other words, they are the data of the time change of the permittivity. The analysis section 42, as will be described later, extracts a parameter indicating the characteristics of the permittivity from the input data of the time change of the permittivity, and analyzes a degree of enhancement of blood coagulation on the basis of a comparison of the extracted parameter with at least one reference value which defines the criteria of the enhancement of blood coagulation.

The analysis section 42 provides notification of information showing the data of the time change of the permittivity and the result of the analysis of the blood coagulation ability based thereon and the like. This notification is performed, for example, by turning the information into a graph and displaying it on a monitor or printing it on a predetermined medium.

The signal processing section 4 may be implemented by a computer. That is, hardware such as CPU (Central Processing Unit), RAM (Random Access Memory) and ROM (Read Only Memory) and software that is necessary for measurement and analysis stored in a memory device (not shown) work together, to realize the functions of each block of the signal processing section 4. Alternatively, the signal processing section 4 may be implemented by PLD (Programmable Logic Device) such as FPGA (Field Programmable Gate Array), or by DSP (Digital Signal Processor), and other devices or the like such as ASIC (Application Specific Integrated Circuit).

2. Blood Coagulation System Analysis Method

An analysis method using the thus configured blood coagulation system analyzer will be described.

(1) About Setting Parameter

Figure 2:
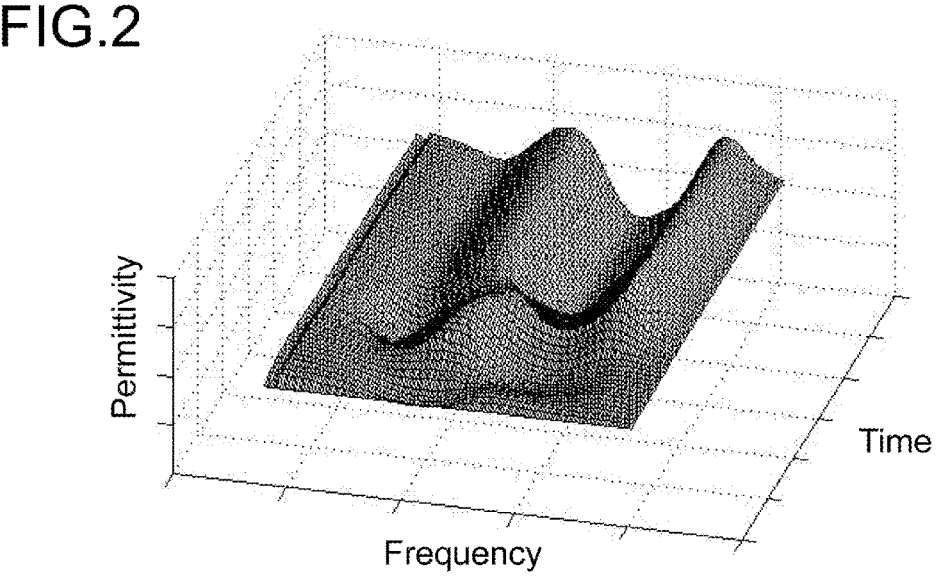
FIG. 2 shows a measurement result by the measurement section, indicating a three-dimensional complex permittivity spectrum which involves time axis.

FIG. 2 shows a measurement result by the measurement section 41, indicating a three-dimensional complex permittivity spectrum which involves time axis. Herein, the vertical axis in FIG. 2 is represented normalized in such a way that the real-number portion of the complex permittivity at each time and each frequency is divided by the real-number portion of the complex permittivity at time zero (immediately after start of measurement) at each frequency.

Figure 3:
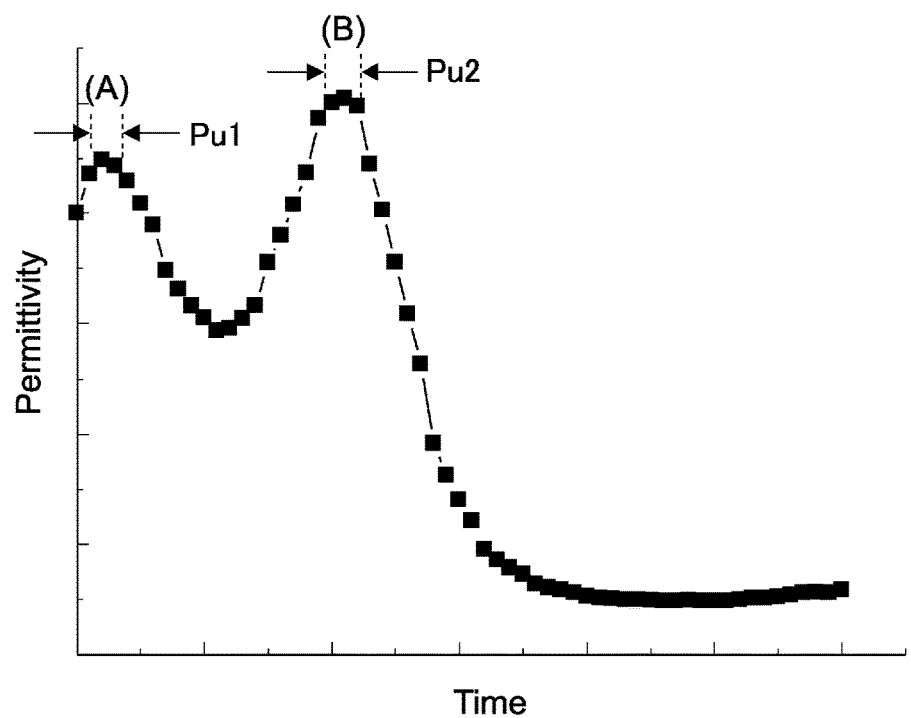
FIG. 3 shows an example of data of a time change of permittivity at a frequency of 760 kHz in a patient.
Figure 4:
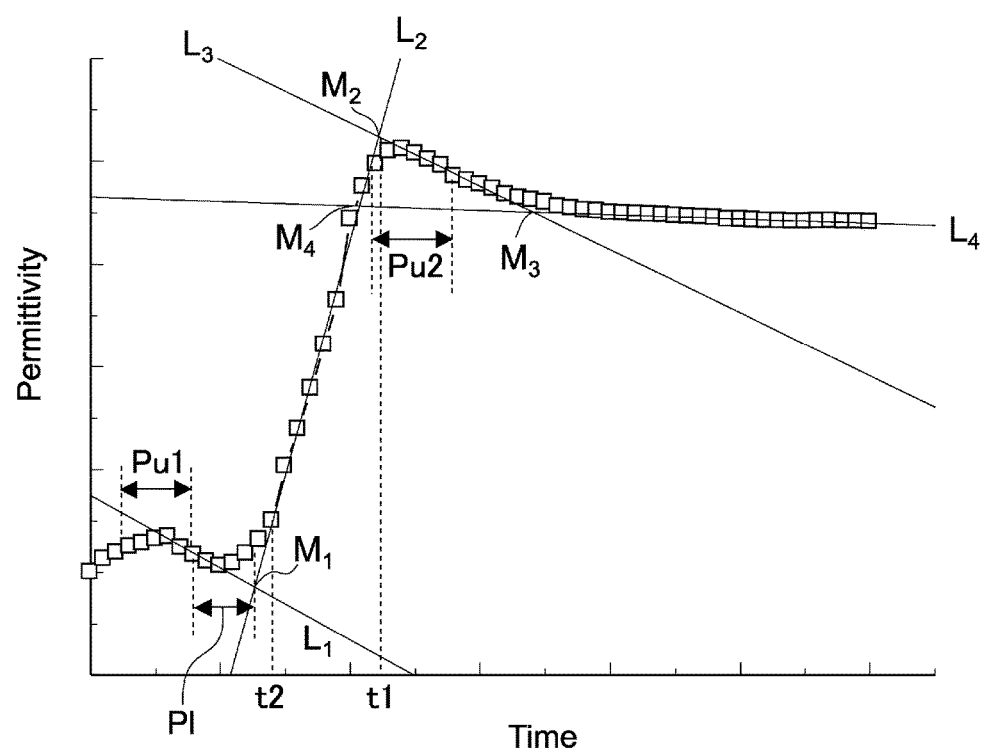
FIG. 4 shows an example of data of the time change of permittivity at a frequency of 10.7 MHz in a patient.
Figure 5:
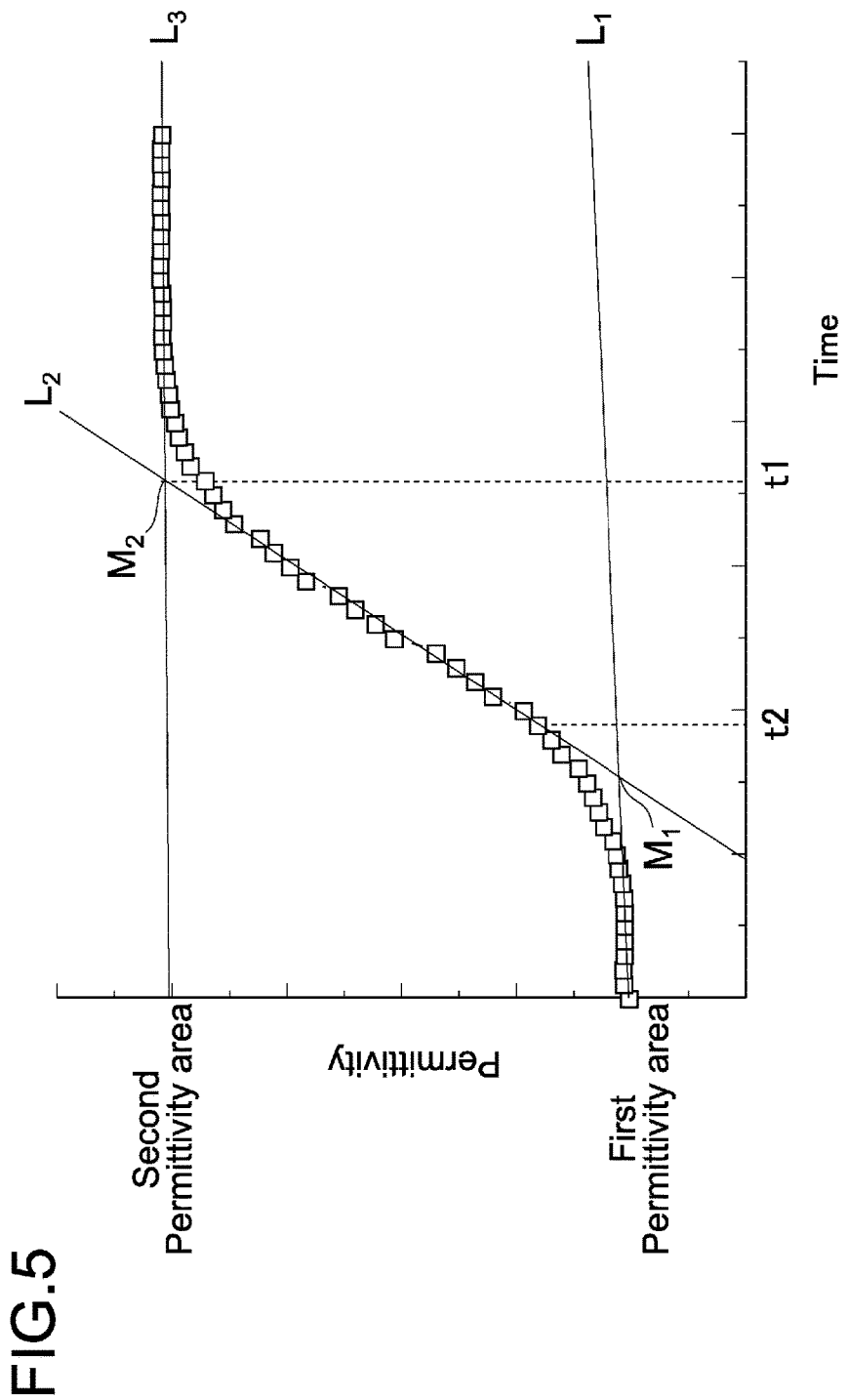
FIG. 5 shows an example of data of the time change of permittivity at a frequency of 10.7 MHz in a healthy subject.

The measurement section 41 outputs data with the axes indicating the permittivity and the time which serve as two-dimensional results out of three-dimensional measurement results, as shown in FIGS. 3 to 5. In other words, it outputs the data of the time change of the permittivity.

The inventors of the present disclosure have revealed in the aforementioned Patent Document 1 that the time change of the permittivity of blood reflects a blood coagulation process. Therefore, the complex permittivity spectrum obtained by this measurement serves as an index for quantitatively indicating the blood coagulation, and thus on the basis of a change thereof, it is possible to obtain information relating to the blood coagulation such as coagulation time, coagulation rate and coagulation intensity.

FIG. 3 shows an example of the three-dimensional spectrum of FIG. 1 being cut out at a frequency, among the frequencies included in the three-dimensional spectrum, of 300 kHz or more and 3 MHz or less and specifically 760 kHz. As shown in FIG. 3, symbol (A) shows a peak associated with rouleau formation of red blood cells, and (B) shows a peak (highest peak value) associated with the blood coagulation process.

FIG. 4 shows an example of the three-dimensional spectrum of FIG. 1 being cut out at a frequency, among the frequencies included in the three-dimensional spectrum, of 2 MHz or more and 40 MHz or less and specifically 10.7 MHz. At the frequency of 10.7 MHz, a stepwise change in the permittivity is seen.

FIG. 5, separately from FIG. 4, shows the time change of permittivity at a frequency of 10.7 MHz with respect to the blood sample of a healthy subject. In this case, such a distinct peak as seen in FIG. 4 of the change in the permittivity is not seen.

From such data of the time change of the permittivity, the analysis section extracts the parameter indicating the characteristics of the permittivity, as mentioned above. As the parameter, various parameters such as the following may be mentioned.

The extrapolated lines drawn on the curve indicating the complex permittivity spectrum (symbols L1 to L4 in FIG. 4);

the coordinates of the intersections of the extrapolated lines (symbols M1 to M4);

the slopes of the extrapolated lines;

the slopes of tangents drawn on the curve indicating the complex permittivity spectrum (derivative value of the permittivity);

a time T that gives a predetermined permittivity E (e.g. maximum value, local maximum value, intermediate value);

a characteristic value obtained by analyzing the time change of the permittivity, the three-dimensional complex permittivity spectrum or the two-dimensional complex permittivity spectrum as an image pattern;

a characteristic value obtained by parameter fitting with use of a function expression capable of reconfiguring the image pattern;

a characteristic value obtained by cluster analysis with use of a large number of data among the spectrum data; and combinations of at least two of the above.

The inventors of the present disclosure have focused on the "time" (characteristic time) indicating the characteristics of the permittivity, among these parameters. The analysis section compares the extracted characteristic time with at least one reference value set in advance, and on the basis of information obtained as a result of the comparison, it analyzes a degree of enhancement of blood coagulation. As the characteristic time for example, as described in the following, the "coagulation time" or the "onset time" is defined.

A. Coagulation Time

As shown in FIGS. 3 and 4, these data of the time change of the permittivity include a second upper peak area Pu2 which is the next peak area of the time (time area) corresponding to a first upper peak area Pu1 which is an early peak area. A "coagulation time" is the time (time area) at which the second upper peak area is reached. At least at frequencies of 300 kHz or more and 3 MHz or less, and 2 MHz or more and 40 MHz or less, the coagulation time is the area including the local maximum value of the data and also the area including the maximum value of the data.

The "upper peak area" herein is an area, regarding the permittivity, which area lies between the peak value (the local maximum value) included in the peak area and the value of −3% to −5% from that peak value. This range "−3% to −5%" shows, in the change in the permittivity at the frequency of interest (as 10.7 MHz in FIG. 4), the percentage when the range between the local minimum value included in a lower peak area (which will be described later) and the local maximum value included in the second upper peak area Pu2 is defined as 100%.

However, as shown in FIG. 5, when the data of the time change of the permittivity were obtained in ramp form, the coagulation time would be the time at the intersection M2 of the extrapolation line L2 (first extrapolation line) and the extrapolation line L3 (second extrapolation line).

As the extrapolation line L2, the line that is inserted in such a way that the slope thereof becomes the maximum at the interval between a first permittivity area and a second permittivity area having higher permittivity than that, which interval is with the largest change of the permittivity (width on the vertical axis), is selected. In order to reduce the influence of variations (noise) in the measured data, the line L2 may be determined in such a way that the slope thereof becomes the maximum after proper smoothing processing is performed.

On the other hand, the extrapolation line L3 is the line that is inserted in such a way that the slope thereof becomes the minimum at the second permittivity area. In practice, the interval which is "immediately after" the extrapolation line L2 lies at the interval from the time where the measured plots start to deviate until about the lapse of 30 minutes.

In order to reduce the influence of variations (noise) in the measured data, the line L3 may be determined in such a way that the slope thereof becomes the minimum after proper smoothing processing is performed.

B. Onset Time

As shown in FIG. 4, when the data include a lower peak area P1 which is after the first upper peak area and a main linear part (taken along the extrapolation line L2) which is between the first lower peak area and the second upper peak area, an onset time is the start time (t2) of the main linear part. As shown in the figure, the onset time is the start timing of an overlap between the extrapolation line L2 and the permittivity curve (see also FIG. 11).

The "lower peak area" herein is an area, regarding the permittivity, which area lies between the peak value (the local minimum value) included in the peak area and the value of −3% to −5% from that peak value.

However, as shown in FIG. 5, when the data of the time change of the permittivity were obtained in ramp form without the peak values, the onset time would be a start time of an overlap between an extrapolation line and the permittivity curve, which extrapolation line is inserted in such a way that the slope thereof becomes the maximum at the interval between a first permittivity area and a second permittivity area having higher permittivity than the first permittivity area.

Alternatively, in the cases as shown in FIG. 5, the onset time may be the time at the intersection M1 between the extrapolation lines L1 and L2. In this case, the extrapolation line L1 may be defined in the same meaning as the extrapolation line L3 in the case of "A. Coagulation time" described above. That is to say, the extrapolation line L1 is the line that is inserted in such a way that the slope thereof becomes the minimum at the first permittivity area.

(2) About Setting Reference Value(s)

In the following, the setting of the "reference value" to be compared with the thus extracted parameters will be described. The inventors of the present disclosure set the reference value on the basis of the study described in the following. In the following study, the above-mentioned "characteristic time" would be employed as the parameter.

A. Experimental example A

In experimental example A, the reference value is set by the each measured value of a healthy subject and hospital patients with respiratory disease (hereinafter referred to as the "patient with respiratory disease").

A-1. About Blood Sampling and Diseases

The inventors of the present disclosure collected blood from the healthy subject by using an evacuated blood collection tube treated with use of sodium citrate as an anticoagulant. This would be the whole blood sample of the healthy subject. In the same manner, the inventors of the present disclosure collected blood from the patient with respiratory disease when the patient is hospitalized. This would be the whole blood sample of the patient with respiratory disease.

Figure 8:
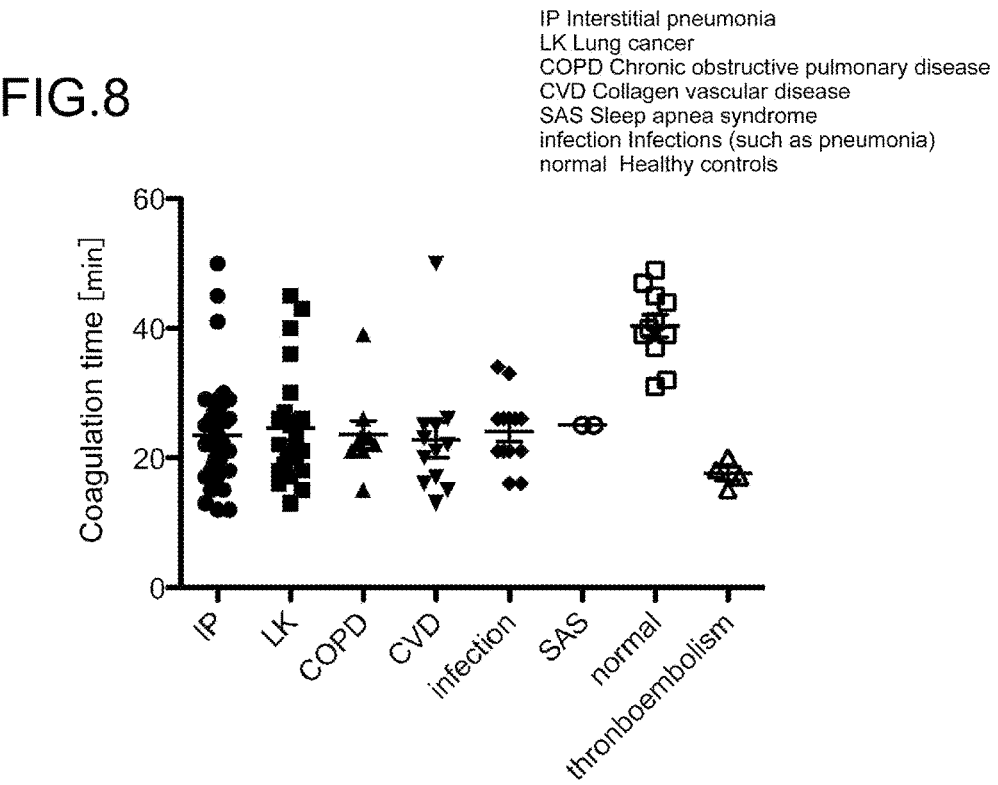
FIG. 8 shows a distribution of the coagulation time in healthy subjects and patients with respiratory disease, in Experimental Example A.

The subject diseases of the patients with respiratory disease herein are classified as interstitial pneumonia (IP), lung cancer (LK), chronic obstructive pulmonary disease (COPD), collagen vascular disease (CVD), sleep apnea syndrome (SAS) or infections such as pneumonia (infection) (see FIG. 8).

In addition, in the cases where the patient developed pulmonary thromboembolism (PE) or deep vein thrombosis (DVT) during hospitalization, these cases were added to the classification of thrombosis (venous thromboembolism (thromboembolism)) (see FIG. 8).

A-2. Dielectric Measurement

The inventors of the present disclosure added 0.25 M of a calcium chloride aqueous solution (85 uL (microliter) per 1 mL of blood) to the blood sample whose temperature was kept at 37° C. and a blood coagulation reaction was started. Immediately after the start of the blood coagulation reaction, the inventors of the present disclosure carried out dielectric measurement (measurement of permittivity) by using the above-described blood coagulation system analyzer, at a temperature of 37° C., a frequency range of 100 Hz to 40 MHz and at measurement time interval of one minute, for 60 minutes in total.

Figure 6:
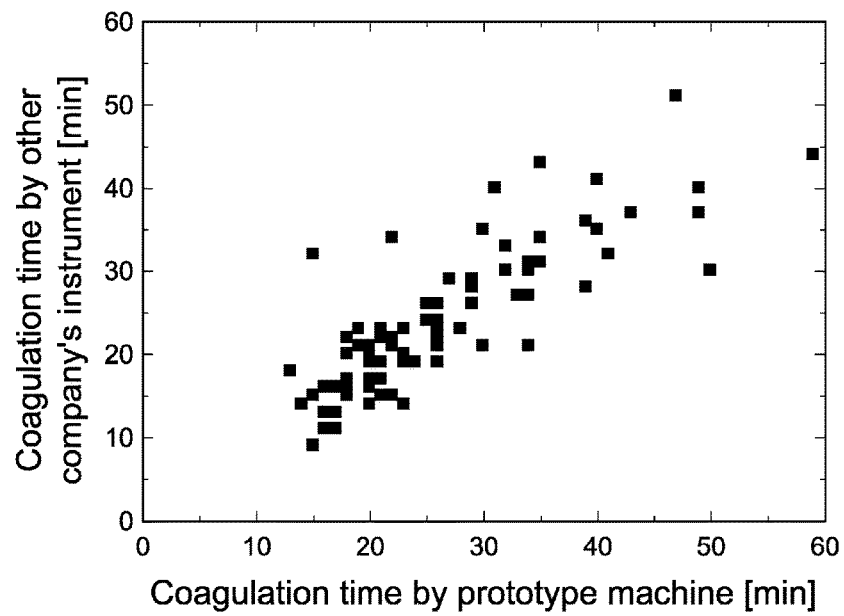
FIG. 6 shows an example of measurement results by a prototype machine of own company and a machine of other company.

As the blood coagulation system analyzer, a dielectric coagulometer prototype machine (produced by Sony Corporation) was used. In FIG. 6, it has been demonstrated that the coagulation time obtained by this dielectric coagulometer prototype machine is in good agreement with the coagulation time according to an impedance analyzer (produced by Agilent Corporation, 4294A) used in Japanese Patent Application Laid-open No. 2010-181400.

A-3. Result

Figure 7:
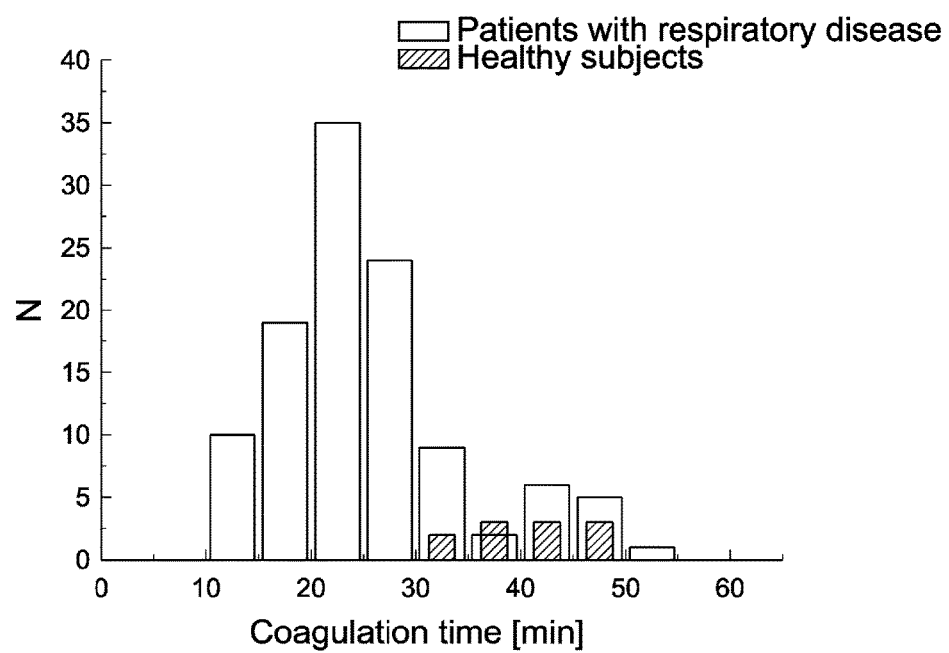
FIG. 7 shows a frequency distribution of coagulation time in healthy subjects and patients with respiratory disease.
Figure 9:
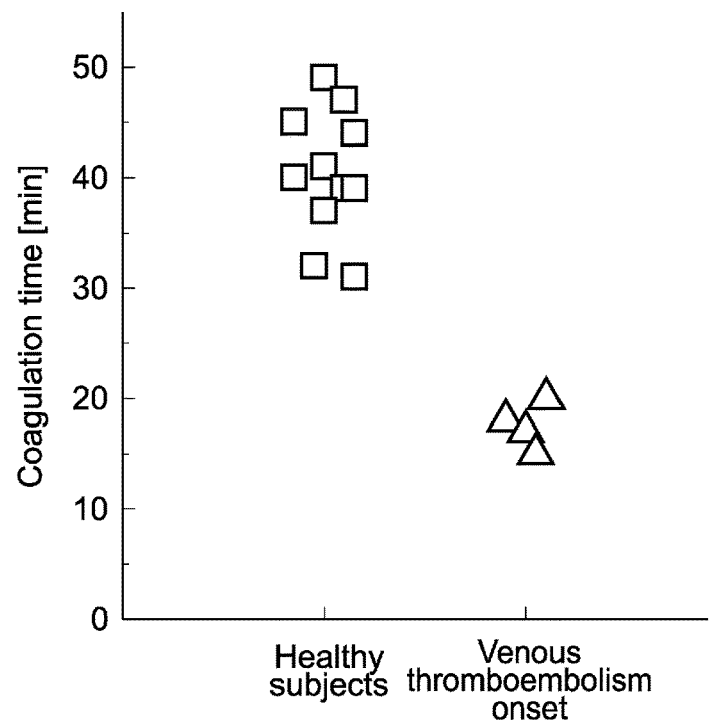
FIG. 9 shows a distribution of the coagulation time in the patients who developed venous thromboembolism, of the patients with respiratory disease in FIG. 8, as compared to that of the healthy subjects.

FIG. 7 shows a frequency distribution of coagulation time in healthy subjects and patients with respiratory disease. The coagulation time herein is one from the data of the time change of the permittivity at a frequency of 10.7 MHz, which is the time at the intersection M2 (the intersection the extrapolation lines L2 and L3) shown in FIG. 4. The intersection M2 is the time included in the time area that corresponds to the above-mentioned second upper peak area. In addition, the coagulation time may be defined also as the time at this point M2. FIG. 8 shows the coagulation time in healthy subjects and patients with respiratory disease, by each disease. Further, FIG. 9 shows a distribution of the coagulation time in the patients who developed thrombosis (venous thromboembolism), of the patients with respiratory disease in FIG. 8, as compared to that of the healthy subjects.

As is clear from these graphs, while the coagulation times of the healthy subjects were within the range of about 30 to 60 minutes, the coagulation times of the patients with respiratory disease were distributed largely in the range of shorter time than 30 minutes. In other words, this shows that the patients with respiratory disease are the patients at higher risk of thrombosis due to enhancement of blood coagulation. In particular, the coagulation times of the patients who actually developed DVT or PE among the patients with respiratory disease, were not more than 20 minutes.

From these facts, we are able to find the reference value which serves as the criteria of how the "degree of the enhancement of blood coagulation" is. From the fact that the coagulation time of the healthy subject was 30 minutes or more, and from the fact that the patient with venous thromboembolism was not more than 20 minutes, the reference value may be set to the time from 20 to 30 minutes (2/3 or more and 3/3 or less).

The reference value may be set as any one of the time from 20 to 30 minutes such as 30 minutes, 27 minutes or 24 minutes. When the obtained coagulation time is greater than the reference value, the analysis section is able to determine, such as that the enhancement of blood coagulation is low and there is little or no risk of thrombosis, and able to provide a notification thereof. On the other hand, when the obtained coagulation time is not more than the reference value, the analysis section is able to determine, such as that the enhancement of blood coagulation is high and there is some risk or high risk of thrombosis, and able to provide a notification thereof.

Alternatively, the reference values may be set by a plurality of stages. For example, there may be the first reference value set to 30 minutes (3/3) and the second reference value set to 20 minutes (2/3). In this case, when the obtained coagulation time is greater than the first reference value, the analysis section is able to determine, such as that the enhancement of blood coagulation is low and there is no risk of thrombosis, and able to provide a notification thereof. On the other hand, when the obtained coagulation time is greater than the second reference value but not more than the first reference value, which is the case where the coagulation time is 20 minutes or more and 30 minutes or less (2/3 or more and 3/3/or less), the analysis section is able as follows. That is, in this case, the analysis section is able to determine, such as that there can be seen some enhancement of blood coagulation and there is more or less risk of thrombosis, and able to provide a notification thereof. Furthermore, when the obtained coagulation time is not more than the second reference value, the analysis section is able to determine, such as that the enhancement of blood coagulation is high and there is high risk of thrombosis, and able to provide a notification thereof.

The information of the reference value(s) that is set in this manner may be stored in the memory device (not shown) in advance. The blood coagulation system analyzer may have this memory device, and otherwise the other equipment which is accessible to the blood coagulation system analyzer may have this memory device. The analysis section obtains the reference value from the memory device, at the time of performing the analysis process.

In addition, the reason why the analysis section uses the ratio such as the above-mentioned "2/3 or more and 3/3/or less" as the reference value(s) is as follows.

The "most appropriate reference value" holds in the cases where only the calcium solution, for example, is added to the blood coagulation as an initiator, and the other coagulation activation factors has been eliminated as much as possible in the measurement. Conversely, it is also possible to shorten the reference value by intentionally causing mild coagulation activation. As methods therefor, for example, adding a certain amount of (trace) coagulation activator (tissue factor, contact factor activator or the like) to the blood, or using a metal or plastic material with high coagulation activation effect as the material of the sample cartridge 2, and the like can be mentioned.

For this reason, the coagulation time depends also on coagulation activation factors, and thus when compared with the case where the coagulation activation factor is not intentionally added to the blood coagulation time, the coagulation time becomes shorter. Therefore, it is desirable to use ratios as the reference value(s).

The characteristic time (coagulation time in this case) of the healthy subject may be preset to 30 minutes as an invariant time, or may be set as a variable time. In the latter case, since the value may vary depending also on coagulation activation factors as described above, by taking this into account, the characteristic time of the healthy subject may be re-measured and be set again at an arbitrary timing or cycle. The characteristic time of the healthy subject may also be stored in the above-mentioned memory device, and the analysis section may access to the memory device to obtain the characteristic time of the healthy subject.

Meanwhile, although it is believed that enhancement of blood coagulation is a key factor of the risk of venous thrombosis, methods for evaluating the degree of enhancement of blood coagulation in a simple and quantitative way that are put to practical use have not been known up to now. In existing techniques, D-dimer, which is a degradation product of the thrombus, has been attracting attention as a molecular marker related to venous thrombosis. However, a high value for the D-dimer means that the thrombus is already formed, so it may not be suitable in terms of risk evaluation of venous thrombosis. Moreover, it is not yet clearly known whether or not it has sufficient sensitivity. Further, it has been found that D-dimer does not have high specificity for venous thrombosis.

Figure 10:
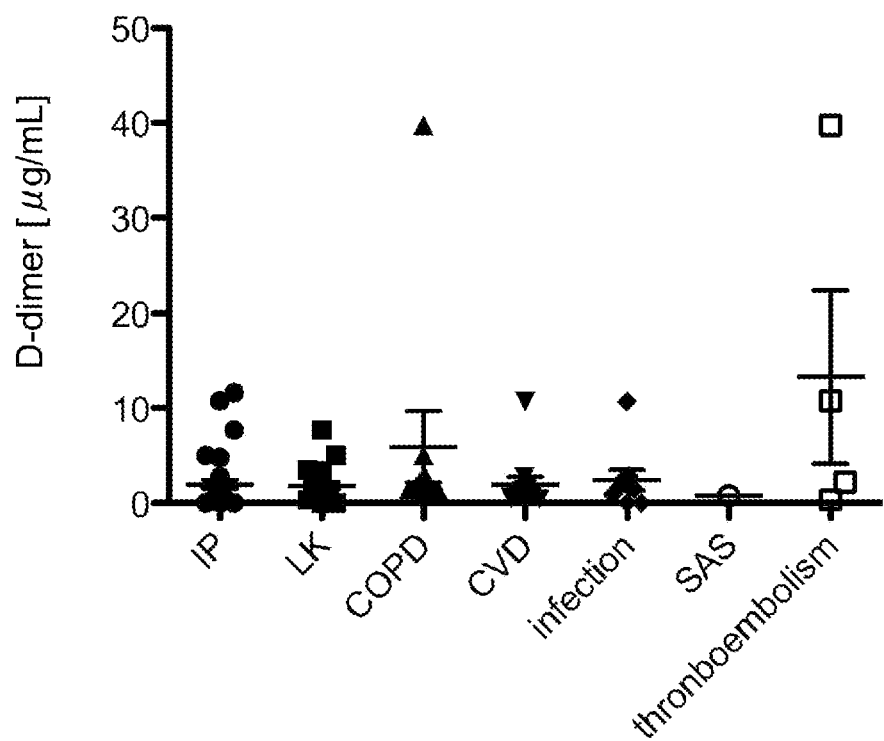
FIG. 10 shows measurement values of D-dimer with respect to the patients with each respiratory disease that is shown in FIGS. 8 and 9.

FIG. 10 shows measurement values of D-dimer with respect to the patients with each respiratory disease that is shown in FIG. 8. D-dimer value is considered to be high in the case of venous thrombosis or the like in general. However, the plots regarding the patients with respiratory disease who actually developed DVT or PE indicate that their D-dimer values ?? are widely distributed from high values to low values.

On the other hand, in the coagulation time shown in FIG. 8 which is able to be obtained by the dielectric measurement as the analysis method of the present disclosure, the coagulation time in every patient with respiratory disease who actually developed DVT or PE is relatively short, so it can be determined to be the hypercoagulable state. This result shows that the dielectric measurement of the present disclosure has higher sensitivity than the D-dimer measurement in evaluating the risk of venous thrombosis and is superior.

Thus, since the present disclosure may analyze the degree of enhancement of blood coagulation based on the time change of permittivity of the blood sample, it is possible to appropriately evaluate the risks associated with it.

As mentioned above, the blood coagulation test method such as PT-INR and APTT, of the related art, was substantially only capable of evaluating the bleeding risk associated with a lowering of the blood coagulation due to excessive administration of the anticoagulant. Furthermore, in the existing platelet aggregation test with use of PRP, the centrifugation procedure is essential, so accurate test result may not be obtained due to that the platelets would be activated in this procedure, and its operation is also cumbersome. According to the present disclosure, it is possible to analyze the degree of enhancement of blood coagulation in the above-described manner, high-precision test result may be obtained, and its operation is also made simple.

Furthermore, the reference value set according to the above-described experimental example A may also be applicable to patients with other internal diseases. In addition, patients with surgical diseases might be more likely to cause thrombosis from the effects of surgery, and thus from the point of view of expanding the range of its risk determination, the reference value is set to a longer time than patients with internal diseases.

Although these results showed an example in which the "coagulation time" was used as the "characteristic time", the similar consideration may be carried out regarding the "onset time".

Figure 11:
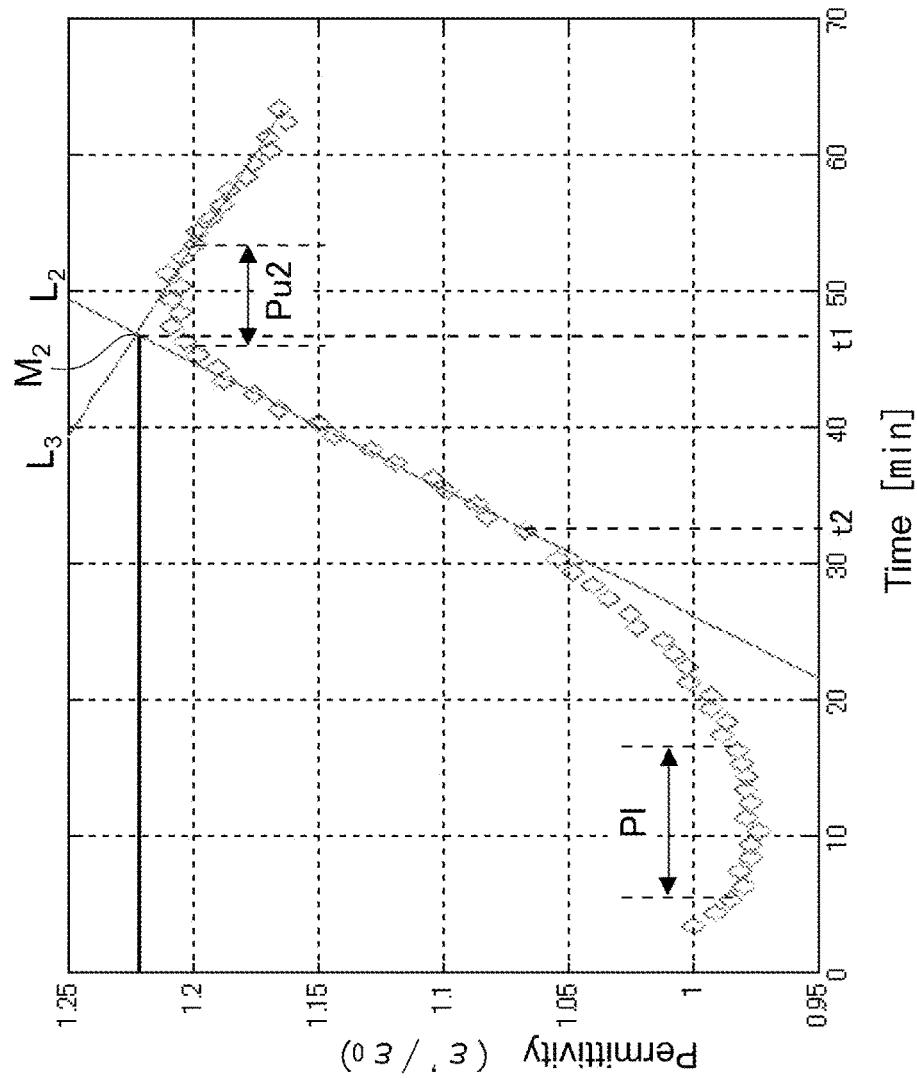
FIG. 11 shows the time change of permittivity at around 10 MHz of the blood collected from a patient with respiratory disease.
Figure 12:
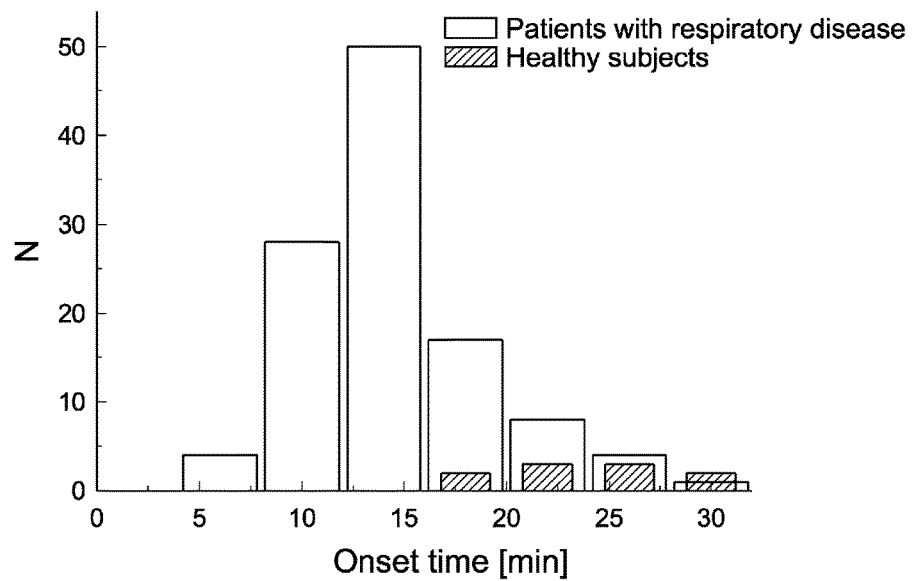
FIG. 12 shows a frequency distribution in healthy subjects and patients with respiratory disease, in which a parameter used out of the parameters each described, is the onset time.

FIG. 11 shows the time change of permittivity at around 10 MHz of the blood collected from a patient with respiratory disease. The extrapolation lines L2 and L3, the intersection M2, the coagulation time t1 and the onset time t2 are shown in this figure. FIG. 12 shows a frequency distribution in healthy subjects and patients with respiratory disease, in which a parameter used out of the parameters each described, is the onset time t2.

As seen from FIG. 12, as with the case where the coagulation time shown in FIG. 7 is set as the parameter, it is shown that the onset times of the patients with respiratory disease were distributed largely in the shorter times than those of the healthy subjects. The onset time would be shorter than the coagulation time, from its definition. The onset times of the healthy subjects were distributed between about 15 minutes and about 40 minutes. From this result, also in the cases where the onset time is used, the reference value, which serves as the criteria of how the "degree of the enhancement of blood coagulation" is, may be set to 15 minutes. When this reference value is represented as a ratio, also the above-mentioned "2/3 or more and 3/3 or less" may be applied as the reference value.

B. Experimental Example B

In experimental example B, in the field of surgery, and specifically by the cases of onset of DVT and PE after an artificial knee joint replacement, the reference value is set.

B-1. About Blood Sampling and Diseases

Artificial knee joint replacement is surgery which carries a very high risk of developing deep vein thrombosis (DVT) after surgery. In the morning of the day of surgery (before surgery) and on day after surgery (postoperatively), blood was collected from the patient by using an evacuated blood collection tube treated with use of sodium citrate as an anticoagulant, and the blood was used for the measurement. An examination of the onset of DVT was carried out by ultrasound examination at 4-5 days after surgery. In the same manner, blood was also collected from the healthy subject by using an evacuated blood collection tube treated with use of sodium citrate as an anticoagulant, and the blood was used for the measurement.

B-2. Dielectric Measurement

The inventors of the present disclosure added 0.25 M of a calcium chloride aqueous solution (85 uL (microliter) per 1 mL of blood) to the blood sample whose temperature was kept at 37° C. and a blood coagulation reaction was started. Immediately after the start of the blood coagulation reaction, the inventors of the present disclosure carried out the measurement by using the above-mentioned dielectric coagulometer prototype machine, at a temperature of 37° C., a frequency range of 100 Hz to 40 MHz and at measurement time interval of one minute, for 60 minutes in total.

B-3. Result

Six cases out of eleven cases had developed DVT.

The inventors of the present disclosure defined the intersection M2 shown in FIGS. 4 and 11 as the coagulation time, using data of the time change of permittivity at around a frequency of 10 MHz.

The mean of the coagulation times of the patients who developed DVT (postoperatively) was 19 minutes, and the mean of those of the patients who did not develop DVT was 22 minutes. Among the patients who developed DVT, the case of the longest coagulation time was 26 minutes. However, it is a special case, because this patient was observed to have DVT from before the surgery. Except for this special case, the case of the longest coagulation time among the patients who developed DVT was 23 minutes.

From these results, as the reference value for determining whether or not the risk of venous thrombosis would increase significantly, the value as the most appropriate value may be set to 26 minutes. In the patients who did not develop DVT, there are many cases with the coagulation time shorter than 26 minutes. However in these cases, although they did not develop DVT as a result, it was a matter of luck, and is originally supposed to be at higher risk.

Figure 13:
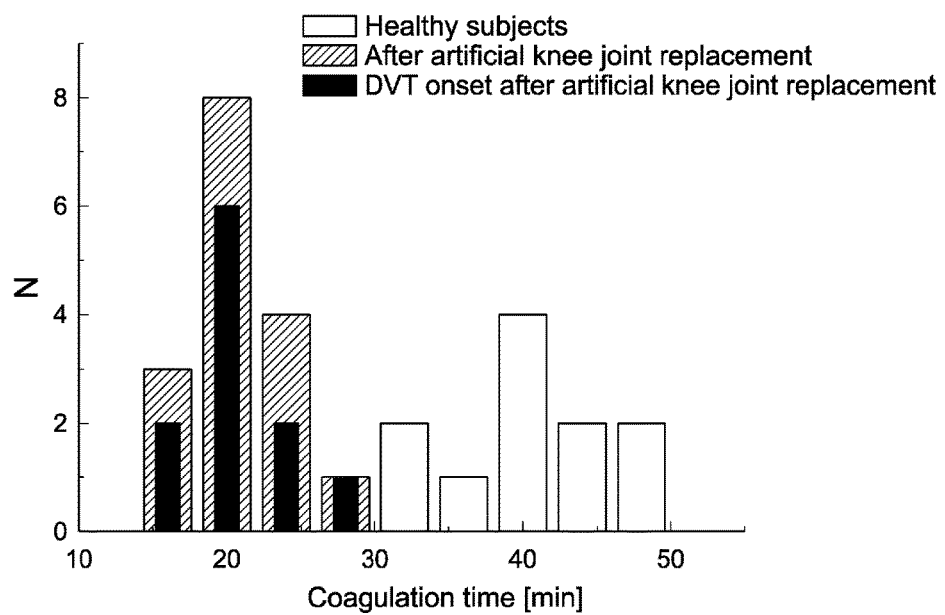
FIG. 13 shows a frequency distribution of the coagulation time in healthy subjects, postoperative patients and patients who developed DVT (deep vein thrombosis) after surgery.

FIG. 13 shows a frequency distribution of the coagulation time in healthy subjects, postoperative patients and patients who developed DVT after surgery. As with the case of experimental example A, the coagulation times of the healthy subjects were 30 minutes or more. Thus, from the fact that the coagulation times of the healthy subjects were 30 minutes or more, and from the fact that the longest coagulation time among those of the patients who developed DVT was 26 minutes, by representing this as a ratio, 26/30 (=13/15) may be set as the reference value. Alternatively, by taking into account the above-mentioned 23 minutes, 23/30 may be set as the reference value.

In other words, one of the time of 23/30 or more and 30/30 or less may be set as the reference value. Alternatively, a plurality in stages, of the time of 23/30 or more and 30/30 or less may be set as a plurality of reference values in stages.

In the perioperative period, it would thus be important to prevent thrombosis because the risk of venous thrombosis increases, but sufficient hemostatic ability is necessary at the time of surgery. Furthermore, blood coagulation in perioperative patients changes every moment, in general. Therefore, on the patients who have scheduled to undergo surgery, by performing a test by the blood coagulation system analyzer according to the present disclosure at first, it may be determined whether or not the risk of thrombosis is high, and also, whether or not the function of platelet is normal.

Depending on the result of the determination, it allows a doctor to comprehensively consider the status of each patient (type and size of the scheduled surgery, or other factors such as diseases) such that the amount of dosage and the like may be carefully decided, which decision may be made easier.

In the perioperative period where the blood coagulation activity changes every moment, the doctor may regularly carry out a permittivity-based coagulation test in combination with any existing test (such as PT-INR and APTT), which allows the doctor to control the amount of dosage as necessary so as to avoid both the risk of thrombosis and the risk of bleeding tendency.

C. Experimental Example C

Experimental example C will describe a medication monitoring in patients with diabetes.

C-1. Experimental Method

The inventors of the present disclosure carried out the study using the blood samples, which are collected respectively from healthy subjects and the patients with diabetes. In the blood sampling, blood from the healthy subject was collected by using an evacuated blood collection tube treated with use of sodium citrate as an anticoagulant. The inventors of the present disclosure added 0.25 M of a calcium chloride aqueous solution (85 uL (microliter) per 1 mL of blood) to the blood sample whose temperature was kept at 37° C. and a blood coagulation reaction was started. The inventors of the present disclosure carried out the measurement by using the impedance analyzer produced by Agilent Corporation, (4294A), at a temperature of 37° C., a frequency range of 40 Hz to 110 MHz and at measurement time interval of one minute, for 60 minutes in total.

C-2. Analysis of Blood Coagulation Time

The data of the time change of permittivity at a frequency of 760 kHz obtained as a result of this dielectric measurement were used.

C-3. Result

FIG. 14 shows a frequency distribution of the coagulation time in the healthy subjects and the patients with diabetes. In FIG. 14, among the patients with diabetes, the frequency of the patients who have been subjected to antiplatelet therapy (five cases) out of the patients who were known whether or not being under antiplatelet therapy (administration of an anti-platelet aggregation drug) (fifteen cases) is also shown.

From this result as well, the at least one reference value for determining the degree of the enhancement of blood coagulation may be set to at least one of the time of 2/3 or more and 3/3 or less.

Diabetes is considered to be causing enhancement of blood coagulation, often causing vascular endothelial dysfunction, and this is supported by the result shown in FIG. 14. That is to say, it can be seen that the coagulation time of the majority of the patients with diabetes is not more than 25 minutes, and thus they are at higher risk of thrombosis.

As mentioned above, in the patients with diabetes in this study, the patients receiving anti-platelet aggregation therapy are included in the high thrombotic risk group. It indicates that regarding these patients, antiplatelet therapy alone may be not enough and it may be better to combine anticoagulant therapy in treating them.

Furthermore, it can be seen that many of the patients with diabetes have not received medication by anti-platelet aggregation drugs or anticoagulants while belonging to the high thrombotic risk group. It can be said that in the test method of the past it was very difficult to quantitatively evaluate the enhancement of blood coagulation, which has been an overlooked risk until now.

In addition, examples of the drugs used for antiplatelet therapy include besides the above-mentioned anti-platelet aggregation drug, also those which are classified as anticoagulants.

(Other Embodiments)

The present disclosure is not limited to the embodiments described above and can be modified without departing from the gist of the present disclosure.

FIG. 15 shows the mean values and the standard deviations of the coagulation time in healthy subjects and patients with each disease. As the patients, from the top, patients developing venous thromboembolism in respiratory, the whole group of patients in orthopedic and patients developing venous thromboembolism in orthopedic, and the whole group of patients with diabetes are listed. From these statistics, the reference value may be set. In addition to the mean value and the standard deviation, there may also be set as the reference value at least one of the median, the maximum value and the minimum value (Needless to say, the maximum value and the minimum value were used in the above experimental examples A to C.). By using such statistical values, it is possible to increase the certainty of the evaluation of the risks due to the hypercoagulable state.

The analysis section may extract at least one of these statistical values and set the reference value by calculation using a predetermined algorithm.

The measurement section in the embodiments described above has calculated the permittivity (complex permittivity). However, there are also quantities which are electrically equivalent to the complex permittivity, including complex impedance, complex admittance, complex capacitance, and complex conductance. They can be converted to each other by simple electrical quantity conversion. Furthermore, measurement of the "complex permittivity" encompasses also measurements of only the real-number portion and of only the imaginary-number portion.

In the above description, the "characteristic time" (coagulation time, onset time) was used as the parameter. However, the scope of the present disclosure is that the same consideration as above is carried out with use of the above-mentioned various parameters among those regarding the time change of impedance (time change of permittivity).

In the above description, the frequency at which the data of three-dimensional spectrum has been cut out was such as 760 kHz and 10.7 MHz, and data of the time change of the permittivity on such only a single frequency were used. However, there may also be used some data of the time change of permittivity (impedance) with respect to a plurality of frequencies, and by an analysis combining parameters that are extracted therefrom, the analysis accuracy may be improved.

As also described in the above, in the data having some peak as shown in FIG. 3 (or, also FIGS. 4 and 11) (the data that are not in ramp form as those shown in FIG. 5), the coagulation time or the onset time may be defined with the extrapolation lines L1 to L3 as set for the data in ramp form. In other words, from within the data having some peak as shown in such as FIG. 3, the line that is inserted in such a way that the slope thereof becomes the maximum at the interval with the largest change of the permittivity would be the extrapolation line L2. Further, the lines each of which are inserted in such a way that the slope thereof becomes the minimum at each interval immediately before and after the interval corresponding to the extrapolation line L2 would be respectively the extrapolation lines L1 and L3. In this case as well, in order to reduce the influence of variations (noise) in the measured data, the line L2 (or L3) may be determined in such a way that the slope thereof becomes the maximum (or minimum), after proper smoothing processing is performed The present disclosure may also be configured as follows.

(1) A blood coagulation system analyzer, including:
a measurement section configured to measure a time change of impedance of a blood sample which is obtainable by applying an alternating electric field to the blood sample; and
an analysis section configured
to extract a parameter indicating the characteristics of the impedance from the measured data of the time change of the impedance, and
to analyze a degree of enhancement of blood coagulation on the basis of a comparison of the extracted parameter with at least one reference value which defines the criteria of the enhancement of blood coagulation.

(2) The blood coagulation system analyzer according to (1), in which
the measurement section is configured to calculate permittivity on the basis of the measured impedance and obtain a time change of the permittivity, and
the analysis section is configured to perform the analysis using a characteristic time which is the time indicating the characteristics of the permittivity as the parameter.

(3) The blood coagulation system analyzer according to (2), in which
the analysis section is configured to obtain the characteristic time of a healthy subject and obtain one of the time of 2/3 or more and 3/3 or less of the characteristic time of the healthy subject as the reference value.

(4) The blood coagulation system analyzer according to (2), in which
the analysis section is configured to obtain reference values which are set by a plurality of stages as the reference values.

(5) The blood coagulation system analyzer according to (4), in which
the analysis section is configured to obtain the characteristic time of a healthy subject and obtain a plurality of the time of 2/3 or more and 3/3 or less of the characteristic time of the healthy subject as the reference values.

(6) The blood coagulation system analyzer according to (3) or (5), in which
the analysis section targets as a determination target the blood sample collected from a patient having respiratory disease, diabetes, or other internal disease.

(7) The blood coagulation system analyzer according to (2), in which
the analysis section is configured to obtain the characteristic time of a healthy subject and obtain one of the time of 23/30 or more and 30/30 or less of the characteristic time of the healthy subject as the reference value.

(8) The blood coagulation system analyzer according to (4), in which
the analysis section is configured to obtain the characteristic time of a healthy subject and obtain a plurality of the time of 23/30 or more and 30/30 or less of the characteristic time of the healthy subject as the reference values.

(9) The blood coagulation system analyzer according to (7) or (8), in which
the analysis section targets as a determination target the blood sample collected from a patient who has undergone an artificial knee joint replacement or other surgery, or collected from a patient taking an antiplatelet drug or an anticoagulant.

(10) The blood coagulation system analyzer according to any one of (2) to (9), in which
the measurement section is configured to obtain data of the time change of the permittivity, including
a first upper peak area which is an early peak area and
a second upper peak area which is the next peak area of the first upper peak area, and the analysis section is configured to employ as the characteristic time a coagulation time which is the time at which the second upper peak area is possible to be reached.

(11) The blood coagulation system analyzer according to (2), in which
the measurement section is configured to obtain data of the time change of the permittivity in ramp form, including
a first permittivity area and
a second permittivity area having higher permittivity than the first permittivity area, and
the analysis section is configured to employ as the characteristic time a coagulation time which is the time at an intersection of
a first extrapolation line inserted in such a way that the slope thereof becomes the maximum at the interval between the first and the second permittivity areas and
a second extrapolation line inserted in such a way that the slope thereof becomes the minimum at the second permittivity area.

(12) The blood coagulation system analyzer according to any one of (2) to (9), in which
the measurement section is configured to obtain data of the time change of the permittivity, including
a first lower peak area after a first upper peak area which is an early peak area,
a second upper peak area which is the next peak area of the first upper peak area and
a main linear part between the first lower peak area and the second upper peak area, and
the analysis section is configured to employ as the characteristic time a start time of the main linear part.

(13) The blood coagulation system analyzer according to (2), in which
the measurement section is configured to obtain data of the time change of the permittivity in ramp form, including
a first permittivity area and
a second permittivity area having higher permittivity than the first permittivity area, and
the analysis section is configured to employ as the characteristic time a start time of an overlap between
an extrapolation line inserted in such a way that the slope thereof becomes the maximum at the interval between the first and the second permittivity areas and
a curve of the time change of the permittivity.

(14) The blood coagulation system analyzer according to any one of (1) to (11), in which
the measurement section is configured to measure the time change of impedance of the blood sample to which the alternating electric field, having a frequency of 2 MHz or more and 40 MHz or less, or 300 kHz or more and 3 MHz or less, is applied.

(15) The blood coagulation system analyzer according to any one of (1), (2) and (14), in which
the analysis section is configured to obtain, as the at least one reference value, at least one selected from the group consisting of the mean value, the standard deviation, the median, the maximum value and the minimum value, of the parameter in each of a healthy subject and a patient.

(16) The blood coagulation system analyzer according to (1), in which
the measurement section is configured to measure the time change of impedance of the blood sample, which is obtainable by applying the alternating electric field to the blood sample collected from a patient taking an anti-platelet aggregation drug or an anticoagulant.

(17) A blood coagulation system analysis method, including:
applying an alternating electric field to a blood sample;
measuring a time change of impedance of the blood sample obtained by the application of the alternating electric field; and
extracting a parameter indicating the characteristics of the impedance from the measured data of the time change of the impedance, and analyzing a degree of enhancement of blood coagulation on the basis of a comparison of the extracted parameter with at least one reference value which defines the criteria of the enhancement of blood coagulation.

(18) A program configured to cause a computer to perform processes of:
measuring a time change of impedance of a blood sample which is obtainable by applying an alternating electric field to the blood sample; and
extracting a parameter indicating the characteristics of the impedance from the measured data of the time change of the impedance, and analyzing a degree of enhancement of blood coagulation on the basis of a comparison of the extracted parameter with at least one reference value which defines the criteria of the enhancement of blood coagulation.

(19) A blood coagulation system analyzer including:
a blood measurement section configured to measure an impedance of a blood sample; and
a blood analysis section configured to determine a degree of blood coagulation based on the impedance.

(20) The blood coagulation system analyzer according to (19), wherein the degree of blood coagulation includes at least one of a degree of enhancement of blood coagulation, bleeding risk, risk of thrombosis, and risk of a coagulation disorder.

(21) The blood coagulation system analyzer according to any one of (19) or (20), wherein the blood analysis section is configured to determine the degree of blood coagulation by comparing a blood coagulation time based on the impedance to a reference blood coagulation time defined so as to distinguish between a healthy subject and a subject with a medical condition.

(22) The blood coagulation system analyzer according to any one of (19) to (21), wherein the medical condition includes at least one of diabetes, atherosclerosis, cancer, heart disease, respiratory disease, and a surgical procedure.

(23) The blood coagulation system analyzer according to any one of (19) to (22), wherein the blood analysis section is configured to determine the blood coagulation time based on a change in impedance of the blood sample over time.

(24) The blood coagulation system analyzer according to any one of (19) to (23), wherein the blood analysis section is configured to determine whether the degree of blood coagulation is high if the blood coagulation time is less than the reference blood coagulation time.

(25) The blood coagulation system analyzer according to any one of (19) to (24), wherein the reference blood coagulation time is between a first mean time including a first standard deviation time associated with blood coagulation of the healthy subject and a second mean time including a second standard deviation time associated with blood coagulation of the subject with the medical condition.

(26) The blood coagulation system analyzer according to any one of (19) to (25), wherein the first standard deviation is combined with a constant value based on a specified accuracy to distinguish between the healthy subject and the subject with the medical condition

(27) The blood coagulation system analyzer according to any one of (19) to (26), further including:
a sample cartridge configured to hold the blood sample;
a pair of electrodes configured to apply a voltage to the blood sample; and
a power supply configured to provide an alternating-current voltage at a predetermined frequency to the pair of electrodes.

(28) The blood coagulation system analyzer according to any one of (19) to (27), wherein the blood measurement section is configured to determine a permittivity of the blood sample based on the impedance.

(29) A method of determining a degree of blood coagulation including:
measuring an impedance of a blood sample; and
determining the degree of blood coagulation based on the impedance.

(30) The method according to (29), wherein determining the degree of blood coagulation includes comparing a blood coagulation time based on the impedance to a reference blood coagulation time configured to distinguish between a healthy subject and a subject with a medical condition.

(31) The method according to any one of (29) or (30), wherein determining that the degree of blood coagulation is high if the blood coagulation time is less than the reference blood coagulation time.

(32) The method according to any one of (29) to (31), wherein determining the degree of blood coagulation includes:
determining the degree of blood coagulation is high if the blood coagulation time is less than the reference blood coagulation time;
determining the degree of blood coagulation is medium if the blood coagulation time is greater than the reference blood coagulation time and less than a second reference blood coagulation time; and
determining the degree of blood coagulation is low if the blood coagulation time is greater than the second reference blood coagulation time.

(33) The method according to any one of (29) to (32), wherein reference blood coagulation time is two-thirds of the second reference blood coagulation time.

(34) The method according to any one of (29) to (33), wherein the reference blood coagulation time is between a first mean time including a first standard deviation time associated with blood coagulation of the healthy subject and a second mean time including a second standard deviation time associated with blood coagulation of the subject with the medical condition.

(35) The method according to any one of (29) to (34), further including:
measuring the inductance of the blood sample periodically during a medical procedure; and
determining the degree of blood coagulation for different periods of the medical procedure based on the impedance.

(36) A machine-accessible device having instructions stored thereon that are configured when executed to cause a machine to at least:
measure an impedance of a blood sample; and
determine a degree of blood coagulation based on the impedance.

(37) The machine-accessible device according to (36), further including instructions stored thereon that are configured when executed to cause a machine to at least determine the degree of blood coagulation by comparing a blood coagulation time based on the impedance to a reference blood coagulation time that has been determined to distinguish between a healthy subject and a subject with a medical condition.

(38) The machine-accessible device according to any one of (36) or (37), wherein the reference blood coagulation time is between a first mean time associated with blood coagulation of the healthy subject and a second mean time associated with blood coagulation of the subject with the medical condition.

(39) The machine-accessible device according to any one of (36) to (38), further including instructions stored thereon that are configured when executed to cause a machine to at least:
measure the impedance of the blood sample periodically during a medical procedure; and
determine the degree of blood coagulation for different periods of the medical procedure based on the impedance.

(40) The machine-accessible device according to any one of (36) to (39), further including instructions stored thereon that are configured when executed to cause a machine to at least determine the degree of blood coagulation is high when the blood coagulation time is less than the reference blood coagulation time.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

REFERENCE SIGNS LIST 4 signal processing section
41 measurement section
42 analysis section

The invention claimed is:
1. A blood coagulation system analyzer comprising:
a blood measurement section configured to measure an impedance of a blood sample; and
a blood analysis section configured to determine a degree of blood coagulation by comparing a blood coagulation onset time associated with a measurement of the impedance under an alternating electric field ranging from 2 MHz to 40 MHz to a reference blood coagulation onset time defined so as to distinguish between a healthy subject and a subject with a medical condition, wherein the impedance is associated with a permittivity of the blood sample and time dependence of the permittivity under the alternating electric field ranging from 2 MHz to 40 MHz and has a stepwise change between a peak value and a valley value, and wherein the blood coagulation onset time is a start time of a main linear part between the peak value and the valley value, and wherein the blood analysis section is configured to output an analysis result associated with the blood coagulation of the blood sample to a display.

2. The blood coagulation system analyzer of claim 1, wherein the degree of blood coagulation includes at least one of a degree of enhancement of blood coagulation, bleeding risk, risk of thrombosis, and risk of a coagulation disorder.

3. The blood coagulation system analyzer of claim 1, wherein the medical condition includes at least one of diabetes, atherosclerosis, cancer, heart disease, respiratory disease, and a surgical procedure.

4. The blood coagulation system analyzer of claim 1, wherein the blood analysis section is configured to determine the blood coagulation onset time based on a change in impedance of the blood sample over time.

5. The blood coagulation system analyzer of claim 1, wherein the blood analysis section is configured to determine whether the degree of blood coagulation is high if the blood coagulation onset time is less than the reference blood coagulation time.

6. The blood coagulation system analyzer of claim 1, wherein the reference blood coagulation onset time is between a first mean time including a first standard deviation time associated with blood coagulation of the healthy subject and a second mean time including a second standard deviation time associated with blood coagulation of the subject with the medical condition.

7. The blood coagulation system analyzer of claim 6, wherein the first standard deviation is combined with a constant value based on a specified accuracy to distinguish between the healthy subject and the subject with the medical condition.

8. The blood coagulation system analyzer of claim 1, further comprising:
a sample cartridge configured to hold the blood sample;
a pair of electrodes configured to apply a voltage to the blood sample; and
a power supply configured to provide an alternating-current voltage at a predetermined frequency to the pair of electrodes.

9. The blood coagulation system analyzer of claim 1, wherein the blood measurement section is configured to determine a permittivity of the blood sample based on the impedance.

10. A method of determining a degree of blood coagulation comprising:
measuring an impedance of a blood sample;
determining a degree of blood coagulation by comparing a blood coagulation onset time associated with a measurement of the impedance under an alternating electric ranging from 2 MHz to 40 MHz to a reference blood coagulation onset time defined so as to distinguish between a healthy subject and a subject with a medical condition, wherein the impedance is associated with a permittivity of the blood sample and time dependence of the permittivity under the alternating electric field ranging from 2 MHz to 40 MHz and has a stepwise change between a peak value and a valley value, and wherein the blood coagulation onset time is a start time of a main linear part between the peak value and the valley value; and outputting an analysis result associated with the blood coagulation of the blood sample to a display.

11. The method of claim 10, wherein determining that the degree of blood coagulation is high if the blood coagulation onset time is less than the reference blood coagulation time.

12. The method of claim 10, wherein determining the degree of blood coagulation includes:
determining the degree of blood coagulation is high if the blood coagulation onset time is less than the reference blood coagulation onset time;
determining the degree of blood coagulation is medium if the blood coagulation onset time is greater than the reference blood coagulation time and less than a second reference blood coagulation onset time; and
determining the degree of blood coagulation is low if the blood coagulation onset time is greater than the second reference blood coagulation onset time.

13. The method of claim 12, wherein the reference blood coagulation onset time is two-thirds of the second reference blood coagulation onset time.

14. The method of claim 10, wherein the reference blood coagulation onset time is between a first mean time including a first standard deviation time associated with blood coagulation of the healthy subject and a second mean time including a second standard deviation time associated with blood coagulation of the subject with the medical condition.

15. The method of claim 10, further comprising:
measuring the inductance of the blood sample periodically during a medical procedure; and
determining the degree of blood coagulation for different periods of the medical procedure based on the impedance.

16. A machine-accessible device having instructions stored thereon that are configured when executed to cause a machine to at least: measure an impedance of a blood sample;
determine a degree of blood coagulation by comparing a blood coagulation onset time associated with a measurement of the impedance under an alternating electric field ranging from 2 MHz to 40 MHz to a reference blood coagulation onset time that has been determined to distinguish between a healthy subject and a subject with a medical condition, wherein the impedance is associated with a permittivity of the blood sample and time dependence of the permittivity under the alternating electric field ranging from 2 MHz to 40 MHz and has a stepwise change between a peak value and a valley value, wherein the blood coagulation onset time is a start time of a main linear part between the peak value and the valley value; and outputting an analysis result associated with the blood coagulation of the blood sample to a display.

17. The machine-accessible device of claim 16, wherein the reference blood coagulation onset time is between a first mean time associated with blood coagulation of the healthy subject and a second mean time associated with blood coagulation of the subject with the medical condition.

18. The machine-accessible device of claim 16, further comprising instructions stored thereon that are configured when executed to cause a machine to at least:
measure the impedance of the blood sample periodically during a medical procedure; and determine the degree of blood coagulation for different periods of the medical procedure based on the impedance.

19. The machine-accessible device of claim 16, further comprising instructions stored thereon that are configured when executed to cause a machine to at least determine the degree of blood coagulation is high when the blood coagulation onset time is less than the reference blood coagulation onset time.

20. The blood coagulation system analyzer of claim 1, wherein
the blood measurement section is configured to measure a time change of impedance of the blood sample which is obtainable by applying an alternating electric field to the blood sample; and
the blood analysis section is configured
to extract a parameter indicating the characteristics of the impedance from the measured data of the time change of the impedance, and
to analyze a degree of enhancement of blood coagulation on the basis of a comparison of the extracted parameter with at least one reference value which defines the criteria of the enhancement of blood coagulation.

21. The blood coagulation system analyzer of claim 19, wherein
the blood measurement section is configured to calculate permittivity on the basis of the measured impedance and obtain a time change of the permittivity, and
the blood analysis section is configured to perform the analysis using a characteristic time which is the time indicating the characteristics of the permittivity as the parameter.

22. The blood coagulation system analyzer of claim 21, wherein the blood analysis section is configured to obtain the characteristic time of a healthy subject and obtain one of the time of 2/3 or more and 3/3 or less of the characteristic time of the healthy subject as the reference value.

23. The blood coagulation system analyzer of claim 21, wherein the blood analysis section is configured to obtain reference values which are set by a plurality of stages as the reference values.

24. The blood coagulation system analyzer of claim 23, wherein the blood analysis section is configured to obtain the characteristic time of a healthy subject and obtain a plurality of the time of 2/3 or more and 3/3 or less of the characteristic time of the healthy subject as the reference values.

25. The blood coagulation system analyzer of claim 22, wherein the blood analysis section targets as a determination target the blood sample collected from a patient having respiratory disease, diabetes, or other internal disease.

26. The blood coagulation system analyzer of claim 21, wherein the blood analysis section is configured to obtain the characteristic time of a healthy subject and obtain one of the time of 23/30 or more and 30/30 or less of the characteristic time of the healthy subject as the reference value.

27. The blood coagulation system analyzer of claim 23, wherein the blood analysis section is configured to obtain the characteristic time of a healthy subject and obtain a plurality of the time of 23/30 or more and 30/30 or less of the characteristic time of the healthy subject as the reference values.

28. The blood coagulation system analyzer of claim 26, wherein the blood analysis section targets as a determination target the blood sample collected from a patient who has undergone an artificial knee joint replacement or other surgery, or collected from a patient taking an antiplatelet drug or an anticoagulant.

29. The blood coagulation system analyzer of claim 21, wherein the blood measurement section is configured to obtain data of the time change of the permittivity, including a first upper peak area which is an early peak area and a second upper peak area which is the next peak area of the first upper peak area, and the blood analysis section is configured to employ as the characteristic time a coagulation time which is the time at which the second upper peak area is possible to be reached.

30. The blood coagulation system analyzer of claim 21, wherein
the blood measurement section is configured to obtain data of the time change of the permittivity in ramp form, including a first permittivity area and a second permittivity area having higher permittivity than the first permittivity area, and
the blood analysis section is configured to employ as the characteristic time a coagulation time which is the time at an intersection of a first extrapolation line inserted in such a way that the slope thereof becomes the maximum at the interval between the first and the second permittivity areas and a second extrapolation line inserted in such a way that the slope thereof becomes the minimum at the second permittivity area.

31. The blood coagulation system analyzer of claim 21, wherein
the blood measurement section is configured to obtain data of the time change of the permittivity, including a first lower peak area after a first upper peak area which is an early peak area, a second upper peak area which is the next peak area of the first upper peak area and the main linear part between the first lower peak area and the second upper peak area.

32. The blood coagulation system analyzer of claim 21, wherein
the blood measurement section is configured to obtain data of the time change of the permittivity in ramp form, including a first permittivity area and a second permittivity area having higher permittivity than the first permittivity area, and
the blood analysis section is configured to employ as the characteristic time a start time of an overlap between an extrapolation line inserted in such a way that the slope thereof becomes the maximum at the interval between the first and the second permittivity areas and a curve of the time change of the permittivity.

33. The blood coagulation system analyzer of claim 20, wherein the blood analysis section is configured to obtain, as the at least one reference value, at least one selected from the group consisting of the mean value, the standard deviation, the median, the maximum value and the minimum value, of the parameter in each of a healthy subject and a patient.

34. The blood coagulation system analyzer of claim 20, wherein the blood measurement section is configured to measure the time change of impedance of the blood sample, which is obtainable by applying the alternating electric field to the blood sample collected from a patient taking an anti-platelet aggregation drug or an anticoagulant.

* * * * *